United States Patent
Yanagawa et al.

(10) Patent No.: US 9,828,309 B2
(45) Date of Patent: Nov. 28, 2017

(54) METHOD FOR PRODUCING MONOCYCLIC AROMATIC HYDROCARBONS

(75) Inventors: Shinichiro Yanagawa, Tokyo (JP); Yuichiro Fujiyama, Tokyo (JP); Yasuyuki Iwasa, Tokyo (JP); Ryoji Ida, Tokyo (JP); Masahide Kobayashi, Tokyo (JP); Susumu Yasui, Yokohama (JP); Yoshishige Sugi, Yokohama (JP); Atsushi Fukui, Kawasaki (JP); Atsuro Nagumo, Kawasaki (JP)

(73) Assignees: JX Nippon Oil & Energy Corporation, Tokyo (JP); CHIYODA CORPORATION, Tokyo (JP)

( * ) Notice: Subject to any disclaimer, the term of this patent is extended or adjusted under 35 U.S.C. 154(b) by 565 days.

(21) Appl. No.: 14/119,281

(22) PCT Filed: May 24, 2012

(86) PCT No.: PCT/JP2012/063386
§ 371 (c)(1),
(2), (4) Date: Mar. 13, 2014

(87) PCT Pub. No.: WO2012/161281
PCT Pub. Date: Nov. 29, 2012

(65) Prior Publication Data
US 2014/0200378 A1 Jul. 17, 2014

(30) Foreign Application Priority Data

May 24, 2011 (JP) .................................. 2011-115639
May 24, 2011 (JP) .................................. 2011-115641

(51) Int. Cl.
*C07C 4/06* (2006.01)
*C10G 35/06* (2006.01)
(Continued)

(52) U.S. Cl.
CPC ................ *C07C 4/06* (2013.01); *B01D 45/12* (2013.01); *B01J 8/005* (2013.01); *C10G 35/04* (2013.01);
(Continued)

(58) Field of Classification Search
CPC .... C10G 35/04; C10G 35/065; C10G 35/095; C10G 35/10; C07C 15/02; C07C 15/04; C07C 15/06; C07C 15/08; B01D 45/12
See application file for complete search history.

(56) References Cited

U.S. PATENT DOCUMENTS 2,541,635 A * 2/1951 Boyer ...................... B01J 8/189
159/DIG. 3
3,849,294 A * 11/1974 Hansen .................. C10G 11/18
208/103
(Continued)

FOREIGN PATENT DOCUMENTS

JP H03-2128 A 1/1991
JP H03-26791 A 2/1991
(Continued)

OTHER PUBLICATIONS

Extended European Search Report dated Oct. 13, 2014 in EP Application No. 12789136.4.
(Continued)

*Primary Examiner* — Sharon Pregler
*Assistant Examiner* — Alyssa L Cepluch
(74) *Attorney, Agent, or Firm* — Panitch Schwarze Belisario & Nadel LLP

(57) ABSTRACT

Method for producing monocyclic aromatic hydrocarbons includes a cracking and reforming reaction step of obtaining products containing monocyclic aromatic hydrocarbons having 6 to 8 carbon atoms and a heavy fraction having 9 or more carbon atoms by bringing the feedstock oil into contact
(Continued)

with a catalyst for producing monocyclic aromatic hydrocarbons containing crystalline aluminosilicate to cause a reaction, a catalyst separation step of separating and removing the catalyst for producing monocyclic aromatic hydrocarbons together with tricyclic aromatic hydrocarbons contained in the products from a mixture of the products and a small amount of the catalyst for producing monocyclic aromatic hydrocarbons carried by the products, both of which are derived in the cracking and reforming reaction step, and a purification and recovery step of purifying and recovering the monocyclic aromatic hydrocarbons having 6 to 8 carbon atoms which are separated from the products formed in the cracking and reforming reaction step.

5 Claims, 3 Drawing Sheets

(51) Int. Cl.
    *B01D 45/12*     (2006.01)
    *B01J 8/00*     (2006.01)
    *C10G 35/14*     (2006.01)
    *C10G 35/04*     (2006.01)
    *C10G 35/10*     (2006.01)
    *B01J 29/40*     (2006.01)
    *B01J 29/70*     (2006.01)
    *B01J 29/87*     (2006.01)

(52) U.S. Cl.
    CPC ........... *C10G 35/065* (2013.01); *C10G 35/10* (2013.01); *C10G 35/14* (2013.01); *B01J 29/40* (2013.01); *B01J 29/70* (2013.01); *B01J 29/87* (2013.01); *C10G 2300/1044* (2013.01); *C10G 2300/1048* (2013.01); *C10G 2300/301* (2013.01); *C10G 2400/30* (2013.01)

(56) References Cited

U.S. PATENT DOCUMENTS

| 4,640,764 A | | 2/1987 | Hamilton, Jr. | |
| 5,990,366 A | * | 11/1999 | Brown | B01J 29/40 585/475 |
| 2012/0012504 A1 | | 1/2012 | Minami et al. | |
| 2013/0006027 A1 | * | 1/2013 | Yanagawa | C10G 69/08 585/251 |

FOREIGN PATENT DOCUMENTS

| JP | H03-52993 A | | 3/1991 | |
| JP | 2008534737 A | | 8/2008 | |
| JP | 2009-235248 A | | 10/2009 | |
| JP | 2011-032333 A | | 2/2011 | |
| WO | 8204441 A1 | | 12/1982 | |
| WO | 2006104661 A1 | | 10/2006 | |
| WO | 2010109897 A1 | | 9/2010 | |
| WO | 2010109899 A1 | | 9/2010 | |
| WO | 2011001572 A1 | | 1/2011 | |
| WO | WO 2011118753 A1 | * | 9/2011 | ............ C10G 69/08 |

OTHER PUBLICATIONS

Notice of Allowance dated Nov. 17, 2015 in JP Application No. 2011115639.

Int'l Search Report dated Aug. 28, 2012 in Int'l Application No. PCT/JP2012/063386.

* cited by examiner

METHOD FOR PRODUCING MONOCYCLIC AROMATIC HYDROCARBONS

CROSS-REFERENCE TO RELATED APPLICATION

This application is a Section 371 of International Application No. PCT/JP2012/063386, filed May 24, 2012, which was published in the Japanese language on Nov. 29, 2012, under International Publication No. WO 2012/161281 A1, and the disclosure of which is incorporated herein by reference.

TECHNICAL FIELD

The present invention relates to a method for producing monocyclic aromatic hydrocarbons in which monocyclic aromatic hydrocarbons are produced from polycyclic aromatic hydrocarbons.

Priority is claimed on Japanese Patent Application No. 2011-115639, filed May 24, 2011, and Japanese Patent Application No. 2011-115641, filed May 24, 2011, the content of which is incorporated herein by reference.

BACKGROUND ART

Light cycle oil (hereinafter referred to as "LCO"), which is cracked light oil produced using a fluid catalytic cracking unit, contains a large amount of polycyclic aromatic hydrocarbon and has been used as diesel or fuel oil. However, in recent years, there has been a proposal to obtain high-value-added monocyclic aromatic hydrocarbons (for example, benzene, toluene, xylene, ethyl benzene and the like) which can be used as a high-octane gasoline base material or a petrochemical raw material from LCO (for example, refer to Patent documents 1 to 4).

PRIOR ART DOCUMENTS

Patent Documents

[Patent document 1] Japanese Unexamined Patent Application, First Publication No. H3-2128
[Patent document 2] Japanese Unexamined Patent Application, First Publication No. H3-52993
[Patent document 3] Japanese Unexamined Patent Application, First Publication No. H3-26791
[Patent document 4] Pamphlet of PCT International Publication No. WO2010/109899

DISCLOSURE OF INVENTION

Technical Problem

However, methods disclosed in Patent documents 1 to 4 do not exhibit a sufficiently high yield of monocyclic aromatic hydrocarbons having 6 to 8 carbon atoms all the time. That is, in the above methods, a number of relatively-low-value-added byproducts other than the target monocyclic aromatic hydrocarbons having 6 to 8 carbon atoms are produced.

The invention has been made to solve the above problem, and an object of the invention is to provide a method for producing monocyclic aromatic hydrocarbons which can produce monocyclic aromatic hydrocarbons having 6 to 8 carbon atoms at a high yield from a feedstock oil containing a polycyclic aromatic hydrocarbon.

Solution to Problem

The present inventors repeated comprehensive studies to achieve the above object and, consequently, obtained the following finding.

In order to increase the yield of monocyclic aromatic hydrocarbons having 6 to 8 carbon atoms, it is effective to circulate heavy fractions other than target products (monocyclic aromatic hydrocarbons having 6 to 8 carbon atoms) in reaction products to a cracking and reforming reaction step so as to make the heavy fractions mixed with a feedstock oil and undergo a cracking and reforming reaction again. Here, the cracking and reforming reaction refers to a reaction in which monocyclic aromatic hydrocarbons are produced through cracking and reforming using a fluidized bed.

As a result of additional studies based on the above finding, the inventors found that the yield of target products can be further increased by adjusting fractions being circulated, and completed the invention.

First Aspect:

[1] A method for producing monocyclic aromatic hydrocarbons according to a first aspect of the invention is a method for producing monocyclic aromatic hydrocarbons in which monocyclic aromatic hydrocarbons having 6 to 8 carbon atoms are produced from a feedstock oil having a 10 volume percent distillation temperature of 140° C. or higher and a 90 volume percent distillation temperature of 380° C. or lower, includes:

a cracking and reforming reaction step of obtaining products containing monocyclic aromatic hydrocarbons having 6 to 8 carbon atoms and a heavy fraction having 9 or more carbon atoms by bringing the feedstock oil into contact with a catalyst for producing monocyclic aromatic hydrocarbons containing crystalline aluminosilicate to cause a reaction, a catalyst separation step of separating and removing the catalyst for producing monocyclic aromatic hydrocarbons together with tricyclic aromatic hydrocarbons contained in the products from a mixture of the products and a small amount of the catalyst for producing monocyclic aromatic hydrocarbons carried by the products, both of which are derived in the cracking and reforming reaction step, and a purification and recovery step of purifying and recovering the monocyclic aromatic hydrocarbons having 6 to 8 carbon atoms which are separated from the products formed in the cracking and reforming reaction step.

[2] The method for producing monocyclic aromatic hydrocarbons according to [1], in which, in the catalyst separation step, a heavy fraction separated using a separation step of separating the products formed in the cracking and reforming reaction step into a plurality of fractions is brought into contact with the mixture of the products and the catalyst for producing monocyclic aromatic hydrocarbons carried by the products, both of which are derived in the cracking and reforming reaction step, thereby removing the catalyst for producing monocyclic aromatic hydrocarbons from the mixture.

[3] The method for producing monocyclic aromatic hydrocarbons according to [1] or [2], in which the heavy fraction separated using the separation step contains tricyclic aromatic hydrocarbons as a main component.

Second Aspect:

[4] A method for producing monocyclic aromatic hydrocarbons according to a second aspect of the invention is a method for producing monocyclic aromatic hydrocarbons in which monocyclic aromatic hydrocarbons having 6 to 8 carbon atoms are produced from a feedstock oil having a 10 volume percent distillation temperature of 140° C. or higher and a 90 volume percent distillation temperature of 380° C. or lower, includes:

a cracking and reforming reaction step of obtaining products containing monocyclic aromatic hydrocarbons having 6 to 8 carbon atoms and a heavy fraction having 9 or more carbon atoms by bringing the feedstock oil into contact with a catalyst for producing monocyclic aromatic hydrocarbons containing crystalline aluminosilicate to cause a reaction, a catalyst separation step of separating and removing the catalyst for producing monocyclic aromatic hydrocarbons together with tricyclic aromatic hydrocarbons contained in the products from a mixture of the products and the catalyst for producing monocyclic aromatic hydrocarbons carried by the products, both of which are derived in the cracking and reforming reaction step, a separation step of separating at least the monocyclic aromatic hydrocarbons having 6 to 8 carbon atoms and a heavy fraction having 9 or more carbon atoms from a derivative derived in the catalyst separation step, a purification and recovery step of purifying and recovering the monocyclic aromatic hydrocarbons having 6 to 8 carbon atoms which are separated in the separation step, and a recycling step of returning the heavy fraction having 9 or more carbon atoms which is separated in the separation step to the cracking and reforming reaction step.

[5] The method for producing monocyclic aromatic hydrocarbons according to [4], including a hydrogenation reaction step of hydrogenating the heavy fraction having 9 or more carbon atoms which is separated in the separation step before the recycling step, in which, in the recycling step, a hydrogenation reaction product of the heavy fraction having 9 or more carbon atoms obtained in the hydrogenation reaction step is returned to the cracking and reforming reaction step.

[6] The method for producing monocyclic aromatic hydrocarbons according to [5], including a hydrogen recovery step of recovering hydrogen which is generated as a by-product in the cracking and reforming reaction step from products obtained in the cracking and reforming reaction step, and a hydrogen supply step of supplying hydrogen recovered in the hydrogen recovery step to the hydrogenation reaction step.

[7] The method for producing monocyclic aromatic hydrocarbons according to any one of [4] to [6], in which the separation step includes a tricyclic aromatic hydrocarbon supply step of supplying tricyclic aromatic hydrocarbons separated from the derivative which is derived in the catalyst separation step to the catalyst separation step.

Advantageous Effects of Invention

According to the method for producing monocyclic aromatic hydrocarbons of the invention, it is possible to produce monocyclic aromatic hydrocarbons having 6 to 8 carbon atoms at a high yield from a feedstock oil containing a polycyclic aromatic hydrocarbon.

Particularly, since the products derived in the cracking and reforming reaction step and a small amount of the catalyst for producing monocyclic aromatic hydrocarbons carried by the products are separated and removed in the catalyst separation step, it is possible to carry out subsequent treatments without causing a clogging problem or any adverse influence on devices.

BEST MODE FOR CARRYING OUT THE INVENTION

First Embodiment

An embodiment of a method for producing monocyclic aromatic hydrocarbons according to a first aspect of the invention will be described.

Figure 1:
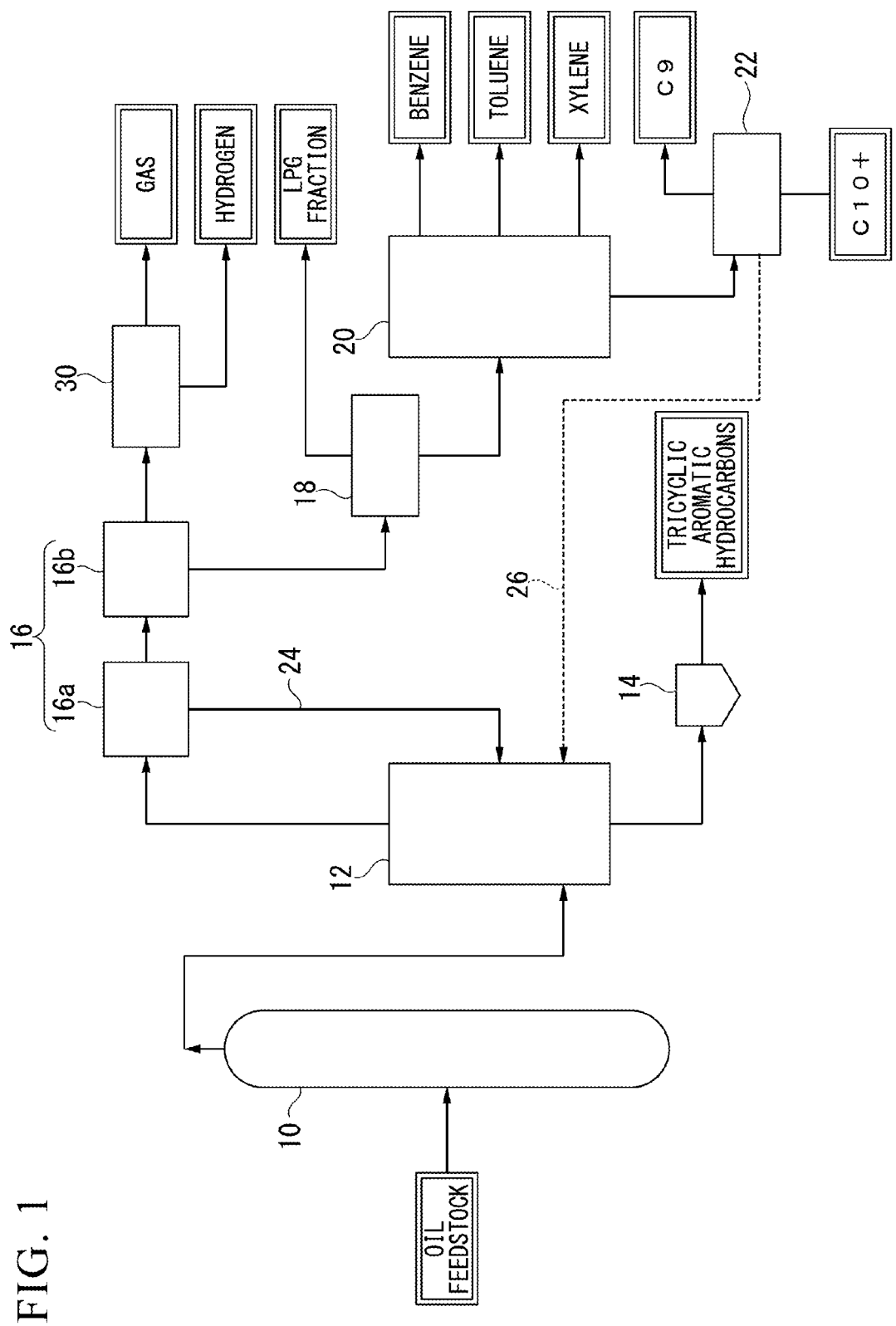
FIG. 1 is a view for describing an embodiment (first embodiment) of a method for producing monocyclic aromatic hydrocarbons according to a first aspect of the invention.

The method for producing monocyclic aromatic hydrocarbons according to the present embodiment is a method for producing monocyclic aromatic hydrocarbons in which monocyclic aromatic hydrocarbons having 6 to 8 carbon atoms are produced from a feedstock oil including the following steps (a) to (f). In addition, FIG. 1 is a schematic configuration view of a production plant for describing the embodiment.

(a) A cracking and reforming reaction step of obtaining products containing monocyclic aromatic hydrocarbons having 6 to 8 carbon atoms and a heavy fraction having 9 or more carbon atoms by bringing a feedstock oil into contact with a catalyst for producing monocyclic aromatic hydrocarbons using a cracking and reforming reactor 10 to cause a reaction.

(b) A catalyst separation step of separating and removing the catalyst for producing monocyclic aromatic hydrocarbons together with tricyclic aromatic hydrocarbons contained in the products using a cleaning tower 12 and a catalyst separation apparatus 14 from a mixture of the products and the catalyst for producing monocyclic aromatic hydrocarbons carried by the products, both of which are derived in the cracking and reforming reaction step.

(c) A separation step of separating at least the monocyclic aromatic hydrocarbons (benzene/toluene/xylene) having 6 to 8 carbon atoms and a heavy fraction having 9 or more carbon atoms from a derivative derived in the catalyst separation step using a first separation apparatus 16 and a second separation apparatus 18, (d) A purification and recovery step of purifying and recovering the monocyclic aromatic hydrocarbons having 6 to 8 carbon atoms which are separated in the separation step using a purification and recovery apparatus 20.

(e) A tricyclic aromatic hydrocarbon supply step of supplying tricyclic aromatic hydrocarbons separated from the derivative which is derived in the catalyst separation step in the separation step to the catalyst separation step using returning lines 24 and 26.

(f) A hydrogen recovery step of recovering hydrogen which is generated as a by-product in the cracking and reforming reaction step from gas components separated in the separation step using a hydrogen recovery apparatus 30.

Among the steps (a) to (f), the steps (a), (b) and (d) are the essential steps of the first aspect, and the steps (c), (e) and (f) are arbitrary steps.

Hereinafter, the respective steps will be specifically described.

<Cracking and Reforming Reaction Step>

In the cracking and reforming reaction step (a), a feedstock oil is introduced into a cracking and reforming reactor 10 filled with a catalyst for producing monocyclic aromatic hydrocarbons, brought into contact with the catalyst for producing monocyclic aromatic hydrocarbons, and reacted with the catalyst. Then, using saturated hydrocarbons contained in the feedstock oil as a hydrogen donor, polycyclic aromatic hydrocarbons are partially hydrogenated through a hydrogen transfer reaction from the saturated hydrocarbons, and the rings are opened, thereby converting the polycyclic aromatic hydrocarbons into monocyclic aromatic hydrocarbons. In addition, the polycyclic aromatic hydrocarbons can be converted into monocyclic aromatic hydrocarbons by cyclizing and dehydrogenating saturated hydrocarbons that are contained in the feedstock oil or obtained in the cracking step. Furthermore, monocyclic aromatic hydrocarbons having 6 to 8 carbon atoms can also be obtained by cracking monocyclic aromatic hydrocarbons having 9 or more carbon atoms.

However, since tricyclic aromatic hydrocarbons have a low reactivity in the cracking and reforming reaction step in spite of being a hydrogenation reaction product, tricyclic aromatic hydrocarbons are rarely converted to monocyclic aromatic hydrocarbons, and, instead, derived together with other products. The products contain hydrogen, methane, ethane, LPG, a heavy fraction having 9 or more carbon atoms, and the like in addition to monocyclic aromatic hydrocarbons.

In addition, in the cracking and reforming reaction step, when the products are derived, a small amount of the catalyst for producing monocyclic aromatic hydrocarbons is derived due to the products carrying the catalyst. Therefore, in the cracking and reforming reaction step, a mixture of the products and the catalyst for producing monocyclic aromatic hydrocarbons is derived from the cracking and reforming reactor 10.

(Feedstock Oil)

A feedstock oil used in the embodiment is an oil having a 10 volume percent distillation temperature of 140° C. or higher and a 90 volume percent distillation temperature of 380° C. or lower. When an oil having a 10 volume percent distillation temperature of lower than 140° C. is used, monocyclic aromatic hydrocarbons are produced from a light oil, and therefore the oil becomes unsuitable for the purpose of the embodiment that produces monocyclic aromatic hydrocarbons from the feedstock oil containing polycyclic aromatic hydrocarbons. In addition, in a case in which an oil having a 90 volume percent distillation temperature of higher than 380° C. is used, the yield of monocyclic aromatic hydrocarbons is lowered such that there is a tendency that the amount of coke sediment on the catalyst for producing monocyclic aromatic hydrocarbons increases and thus the activity of the catalyst abruptly decreases.

The 10 volume percent distillation temperature of the feedstock oil is preferably 150° C. or higher, and the 90 volume percent distillation temperature of the feedstock oil is preferably 360° C. or lower.

The 10 volume percent distillation temperature and the 90 volume percent distillation temperature mentioned herein refer to values measured based on JIS K 2254 "Petroleum Products-Determination of Distillation Characteristics".

Examples of the feedstock oil having a 10 volume percent distillation temperature of 140° C. or higher and a 90 volume percent distillation temperature of 380° C. or lower include light cycle oils (LCO) produced in fluidized catalytic crackers, hydro-refined oils of LCOs, coal-liquefied oils, heavy oil hydrocracking purified oils, straight-run kerosene, straight-run light oils, coker kerosene, coker light oils, oil sand hydrocracking purified oils and the like.

A polycyclic aromatic hydrocarbon is a substance which has a low reactivity and is not easily converted to a monocyclic aromatic hydrocarbon in the cracking and reforming reaction step of the embodiment. However, on the other hand, when hydrogenated in the hydrogenation reaction step, a polycyclic aromatic hydrocarbon is converted to naphthenobenzene, and can be converted to monocyclic aromatic hydrocarbons when supplied back to the cracking and reforming reaction step again for recycling. Therefore, the upper limit of the content of polycyclic aromatic hydrocarbons in the feedstock oil is not particularly limited. However, among polycyclic aromatic hydrocarbons, tri- or more-cyclic aromatic hydrocarbons consume a large amount of hydrogen in the hydrogenation reaction step, and have a low reactivity in the cracking and reforming reaction step even in a hydrogenated form, and therefore the inclusion of a large amount of a polycyclic aromatic hydrocarbon is not preferable. Therefore, the content of tri- or more-cyclic aromatic hydrocarbons in the feedstock oil is preferably 25 volume percent or less, and more preferably 15 volume percent or less.

The feedstock oil which contains bicyclic aromatic hydrocarbons that are converted to naphthenobenzene in the hydrogenation reaction step and have an aim to reduce tri- or more-cyclic aromatic hydrocarbons preferably has a 90 volume percent distillation temperature of, for example, 330° C. or lower.

In addition, the polycyclic aromatic hydrocarbons mentioned herein refer to the total value of the content of bicyclic aromatic hydrocarbons (bicyclic aromatic components) and the content of tri- or more-cyclic aromatic hydrocarbons (tri- or more-cyclic aromatic components) which are measured based on JPI-5S-49 "Petroleum Products-Determination of Hydrocarbon Types-High Performance Liquid Chromatography" or analyzed using FID gas chromatography or two-dimensional gas chromatography. Hereinafter, in a case in which the contents of polycyclic aromatic hydrocarbons, bicyclic aromatic hydrocarbons and tri- or more-cyclic aromatic hydrocarbons are indicated using volume percent, the contents will be values measured based on JPI-5S-49, and, in a case in which the contents are indicated using mass percent, the contents will be values measured based on FID gas chromatography or two-dimensional gas chromatography.

(Reaction Type)

The reaction type when bringing the feedstock oil into contact with the catalyst for producing monocyclic aromatic hydrocarbons to cause a reaction, that is, the reaction type of the cracking and reforming reactor 10 can include a fixed bed type, a moving bed type, a fluidized bed type or the like.

In the embodiment, since a heavy component is used as the raw material, a fluidized bed type is preferable since a coke component deposited to the catalyst can be continuously removed and the reaction can be stably carried out, and a continuous regeneration-type fluidized bed is particularly preferable since the catalyst is circulated between the reactor and a regenerator and the reaction and the regeneration can be continuously repeated. Generally, there are a bed cracking-type fluidized bed and a riser cracking-type fluidized bed; however, in the case of the embodiment, the reaction is desirably carried out under mild conditions using a bed cracking-type fluidized bed. The feedstock oil when brought in contact with the catalyst for producing monocyclic aromatic hydrocarbons is preferably in a gaseous state. In addition, the raw material may be diluted using gas if necessary.

(Catalyst for Producing Monocyclic Aromatic Hydrocarbons)

The catalyst for producing monocyclic aromatic hydrocarbons contains crystalline aluminosilicate.

[Crystalline Aluminosilicate]

The crystalline aluminosilicate is preferably a middle-pore zeolite and/or a large-pore zeolite since the yield of monocyclic aromatic hydrocarbons can be further increased.

The middle-pore zeolite is a zeolite having a skeleton structure with a 10-membered ring, and examples of the middle-pore zeolite include zeolites having AEL type, EUO type, FER type, HEU type, MEL type, MFI type, NES type, TON type and WEI type crystal structures. Among the above zeolites, an MFI-type zeolite is preferable since the yield of monocyclic aromatic hydrocarbons can be further increased.

The large-pore zeolite is a zeolite having a skeleton structure with a 12-membered ring, and examples of the large-pore zeolite include zeolites having AFI type, ATO type, BEA type, CON type, FAU type, GME type, LTL type, MOR type, MTW type and OFF type crystal structures. Among the above zeolites, BEA-type, FAU-type and MOR-type zeolites are preferable due to their industrial applicability, and a BEA-type zeolite is preferable since the yield of monocyclic aromatic hydrocarbons can be further increased.

The crystalline aluminosilicate may contain a small-pore zeolite having a skeleton structure with a 10 or less-membered ring and an ultra large-pore zeolite having a skeleton structure with a 14 or more-membered ring in addition to the middle-pore zeolite and the large-pore zeolite.

Here, examples of the small-pore zeolite include zeolites having ANA type, CHA type, ERI type, GIS type, KFI type, LTA type, NAT type, PAU type and YUG type crystal structures.

Here, examples of the ultra large-pore zeolite include zeolites having CLO type and VPI type crystal structures.

In a case in which a fixed bed-type reaction is employed in the cracking and reforming reaction step, the content of the crystalline aluminosilicate in the catalyst for producing monocyclic aromatic hydrocarbons is preferably in a range of 60% by mass to 100% by mass, more preferably in a range of 70% by mass to 100% by mass, and particularly preferably in a range of 90% by mass to 100% by mass when the content of the entire catalyst for producing monocyclic aromatic hydrocarbons is set to 100% by mass. When the content of the crystalline aluminosilicate is 60% by mass or more, the yield of monocyclic aromatic hydrocarbons can be sufficiently increased.

In a case in which a fluidized bed-type reaction is employed in the cracking and reforming reaction step, the content of the crystalline aluminosilicate in the catalyst for producing monocyclic aromatic hydrocarbons is preferably in a range of 20% by mass to 60% by mass, more preferably in a range of 30% by mass to 60% by mass, and particularly preferably in a range of 35% by mass to 60% by mass when the content of the entire catalyst for producing monocyclic aromatic hydrocarbons is set to 100% by mass. When the content of the crystalline aluminosilicate is 20% by mass or more, the yield of monocyclic aromatic hydrocarbons can be sufficiently increased. When the content of the crystalline aluminosilicate exceeds 60% by mass, the content of a binder that can be incorporated into the catalyst decreases, and thus there are cases in which the catalyst becomes unsuitable for a fluidized bed-type reaction.

[Phosphorous and Boron]

The catalyst for producing monocyclic aromatic hydrocarbons preferably contains phosphorous and/or boron. When the catalyst for producing monocyclic aromatic hydrocarbons contains phosphorous and/or boron, it is possible to prevent the yield of monocyclic aromatic hydrocarbons from decreasing over time, and the generation of coke on the surface of the catalyst can be suppressed.

Examples of a method for adding phosphorous to the catalyst for producing monocyclic aromatic hydrocarbons include a method of supporting phosphorous in the crystalline aluminosilicate, crystalline gallo-aluminosilicate or crystalline zinco-aluminosilicate using an ion-exchange method, an impregnation method or the like, a method of adding a phosphorous compound during the synthesis of a zeolite so as to substitute some of the crystalline aluminosilicate in the skeleton with phosphorous, a method of using a crystallization accelerator containing phosphorous during the synthesis of a zeolite, and the like. A phosphate ion-containing aqueous solution used at this time is not particularly limited, but an aqueous solution prepared by dissolving phosphoric acid, ammonium phosphate dibasic, ammonium dihydrogen phosphate or other water-soluble phosphate at an arbitrary concentration can be preferably used.

Examples of a method for adding boron to the catalyst for producing monocyclic aromatic hydrocarbons include a method of supporting boron in the crystalline aluminosilicate, crystalline gallo-aluminosilicate or crystalline zinco-aluminosilicate using an ion-exchange method, an impregnation method or the like, a method of adding a boron compound during the synthesis of a zeolite so as to substitute some of the crystalline aluminosilicate in the skeleton with boron, a method of using a crystallization accelerator containing boron during the synthesis of a zeolite, and the like.

The content of phosphorous and/or boron in the catalyst for producing monocyclic aromatic hydrocarbons is preferably in a range of 0.1% by mass to 10% by mass, more preferably in a range of 0.5% by mass to 9% by mass, and particularly preferably in a range of 0.5% by mass to 8% by mass when the content of the entire catalyst for producing monocyclic aromatic hydrocarbons is set to 100% by mass. When the content of phosphorous and/or boron with respect to the total mass of the catalyst is 0.1% by mass or more, it is possible to prevent the yield of monocyclic aromatic hydrocarbons from decreasing over time, and, when the content is 10% by mass or less, the yield of monocyclic aromatic hydrocarbons can be increased.

[Gallium and Zinc]

The catalyst for producing monocyclic aromatic hydrocarbons can contain gallium and/or zinc as necessary. When the catalyst for producing monocyclic aromatic hydrocarbons contains gallium and/or zinc, it is possible to increase the generation proportion of monocyclic aromatic hydrocarbons.

Regarding the format of the inclusion of gallium in the catalyst for producing monocyclic aromatic hydrocarbons, the catalyst can contain gallium incorporated into the lattice skeleton of the crystalline aluminosilicate (crystalline aluminosilicate), can contain gallium supported in the crystalline aluminosilicate (gallium-supported crystalline aluminosilicate), or can contain gallium both incorporated into the lattice skeleton of the crystalline aluminosilicate and supported in the crystalline aluminosilicate.

Regarding the format of the inclusion of zinc in the catalyst for producing monocyclic aromatic hydrocarbons, the catalyst can contain zinc incorporated into the lattice skeleton of the crystalline aluminosilicate (crystalline zinco-aluminosilicate), can contain zinc supported in the crystalline aluminosilicate (zinc-supported crystalline aluminosilicate), or can contain zinc both incorporated into the lattice skeleton of the crystalline aluminosilicate and supported in the crystalline aluminosilicate.

The crystalline gallo-aluminosilicate and the crystalline zinco-aluminosilicate have a structure including $SiO_4$, $AlO_4$ and $GaO_4/ZnO_4$ structures in the skeletons. In addition, the crystalline gallo-aluminosilicate and the crystalline zinco-aluminosilicate can be obtained using, for example, gel crystallization through hydrothermal synthesis, a method of inserting gallium or zinc into the lattice skeleton of the crystalline aluminosilicate or a method of inserting aluminum into the lattice skeleton of the crystalline gallo-aluminosilicate or the crystalline zinco-aluminosilicate.

The gallium-supported crystalline aluminosilicate contains gallium supported in the crystalline aluminosilicate using a well-known method such as an ion-exchange method or an impregnation method. A gallium source used at this time is not particularly limited, and examples thereof include gallium salts such as gallium nitrate and gallium chloride, gallium oxides and the like.

The zinc-supported crystalline aluminosilicate contains zinc supported in the crystalline aluminosilicate using a well-known method such as an ion-exchange method or an impregnation method. A zinc source used at this time is not particularly limited, and examples thereof include zinc salts such as zinc nitrate and zinc chloride, zinc oxides and the like.

In a case in which the catalyst for producing monocyclic aromatic hydrocarbons contains gallium and/or zinc, the content of gallium and/or zinc in the catalyst for producing monocyclic aromatic hydrocarbons is preferably in a range of 0.01% by mass to 5.0% by mass, and more preferably in a range of 0.05% by mass to 2.0% by mass when the content of the entire catalyst is set to 100% by mass. When the content of gallium and/or zinc is 0.01% by mass or more, it is possible to increase the generation proportion of monocyclic aromatic hydrocarbons, and, when the content is 5.0% by mass or less, the yield of monocyclic aromatic hydrocarbons can be further increased.

[Shape]

The catalyst for producing monocyclic aromatic hydrocarbons is given, for example, a powder form, a grain form, a pellet form or the like depending on the reaction type. For example, the catalyst is given a powder form in the case of a fluidized bed as in the embodiment, and the catalyst is given a grain form or a pellet form in the case of a fixed bed as in another embodiment. The average grain diameter of the catalyst used in a fluidized bed is preferably in a range of 30 μm to 180 μm, and more preferably in a range of 50 μm to 100 μm. In addition, the bulk density of the catalyst used in a fluidized bed is preferably in a range of 0.4 g/cc to 1.8 g/cc, and more preferably in a range of 0.5 g/cc to 1.0 g/cc.

The average grain diameter refers to the grain diameter located at 50% by mass in a grain diameter distribution obtained by classification using a sieve, and the bulk density is a value measured using the method of Standard No. JIS R 9301-2-3.

In a case in which a grain-form or pellet-form catalyst is obtained, it is possible to incorporate an oxide that is inactive to the catalyst as a binder as necessary and then mold the catalyst using a variety of molding machines.

In a case in which the catalyst for producing monocyclic aromatic hydrocarbons contains an inorganic oxide such as a binder, a phosphorous-containing substance may be used as the binder.

(Reaction Temperature)

The reaction temperature when the feedstock oil is brought into contact with the catalyst for producing monocyclic aromatic hydrocarbons so as to react with the catalyst is not particularly limited, but the reaction temperature is preferably in a range of 400° C. to 650° C. When the lower limit of the reaction temperature is 400° C. or higher, it is possible to facilitate the reaction of the feedstock oil, and the lower limit is preferably 450° C. or higher. In addition, when the upper limit of the reaction temperature is 650° C., it is possible to sufficiently increase the yield of monocyclic aromatic hydrocarbons, and the upper limit is preferably 600° C. or lower.

(Reaction Pressure)

The reaction pressure when the feedstock oil is brought into contact with the catalyst for producing monocyclic aromatic hydrocarbons so as to react with the catalyst is preferably set to 1.5 MPaG or less, and more preferably set to 1.0 MPaG or less. When the reaction pressure is 1.5 MPaG or less, the generation of a byproduct of a light gas can be suppressed, and thus it is possible to use a reaction apparatus with a low pressure resistance.

(Contact Time)

The contact time between the feedstock oil and the catalyst for producing monocyclic aromatic hydrocarbons is not particularly limited as long as a substantially desired reaction proceeds, but is preferably in a range of 1 second to 300 seconds in terms of, for example, the time for gas to pass through the catalyst for producing monocyclic aromatic hydrocarbons, and, furthermore, it is more preferable to set the lower limit to 5 seconds and the upper limit to 150 seconds. When the contact time is 1 second or more, it is possible to ensure the reaction of all the feedstock oil, and, when the contact time is 300 seconds or less, the accumulation of carbonaceous substances on the catalyst due to excessive coking and the like can be suppressed. In addition, the amount of a light gas generated due to decomposition can be suppressed.

<Catalyst Separation Step>

In the catalyst separation step (b), the catalyst is removed from the mixture of the products and the catalyst for producing monocyclic aromatic hydrocarbons (hereinafter, sometimes, simply referred to as catalyst) carried by the products, both of which are derived in the cracking and reforming reaction step (cracking and reforming reactor 10). In addition, the tricyclic aromatic hydrocarbons contained in the products are also separated and removed.

That is, the catalyst separation step is configured to include the cleaning tower 12 to which the mixture is supplied and a catalyst separator 14 that separates a heavy fraction derived from the cleaning tower 12 into solid and liquid so as to separate and remove the catalyst.

The operation in the cleaning tower 12 will be described.

The vapor of the product from the cracking and reforming reactor 10 is supplied to a lower portion of the cleaning tower 12. In the cleaning tower 12, after a tower bottom liquid of the cleaning tower 12 leaks, the pressure is increased using a pump, and the liquid is cooled using a heat exchanger, circulated to the middle of the cleaning tower 12. In the cleaning tower 12, a reaction product of the vapor and the circulated liquid make a countercurrent contact so that catalyst particles which are contained in the reaction product in a small amount and carried from the cracking and reforming reactor 10 are trapped by the circulated liquid, whereby it is possible to remove the catalyst particles from the reaction product. However, the circulated liquid is also circulated, and therefore the circulated liquid in the middle of the cleaning tower 12 also contains a small amount of the catalyst. In a case in which gas and liquid are brought into countercurrent contact with each other, it is not possible to prevent liquid droplets from carrying the catalyst particles, and thus the liquid droplets also contain the catalyst, and therefore, consequently, an extremely small amount of the catalyst remains in the vapor of the reaction product. In order to trap and separate the liquid droplets containing the carried catalyst particles, a heavy fraction separated using the first separation apparatus 16 containing no catalyst and/or a heavy fraction (containing a large amount of tricyclic aromatic hydrocarbons) separated in the purification and recovery step are supplied to the top portion of the cleaning tower 12. As such, the catalyst particles are removed using a two-step treatment in which a majority of the catalyst is removed using the circulated tower bottom liquid in the bottom portion of the cleaning tower 12, and, furthermore, the reaction product of the vapor containing an extremely small amount of the catalyst and the heavy fraction from the first separation apparatus 16 which contains no catalyst are brought into countercurrent contact with each other in the top portion, thereby trapping the liquid droplets containing the catalyst.

The cleaning tower 12, for example, includes a baffle tray in which approximately three theoretical plates are set, and is a machine that separates the catalyst from the product that is cooled and partially liquefied while circulating and cooling the mixture supplied at a high temperature state (for example, 550° C.) in an external cooling machine (not illustrated). In addition, tricyclic aromatic hydrocarbons are supplied to the cleaning tower 12 as a cleaning liquid from the separation step described below. The cleaning liquid cleans the product in a mixed gas-liquid state in the cleaning tower 12 and causes the catalyst contained in the product to be transferred to the cleaning liquid, thereby efficiently separating and removing the catalyst from the product.

In addition, the cleaning tower 12 derives hydrogen, gas components such as methane and ethane, light components such as LPG, monocyclic aromatic hydrocarbons having 6 to 8 carbon atoms, monocyclic aromatic hydrocarbons having 9 or more carbon atoms and some of a heavy fraction having 10 or more carbon atoms from a tower top portion, and also derives heavy fractions such as polycyclic aromatic hydrocarbons, mainly tricyclic aromatic hydrocarbons, or the catalyst from a tower bottom portion. However, since tricyclic aromatic hydrocarbons are supplied to the cleaning tower 12 as the cleaning liquid from the separation step described below, the heavy fraction derived from the tower bottom portion of the cleaning tower 12 contains not all but only some of the tricyclic aromatic hydrocarbons in the mixture in the cleaning tower 12. That is, not all but only some of the tricyclic aromatic hydrocarbons in the mixture in the cleaning tower 12 are derived from the tower bottom portion. The heavy fraction derived from the tower bottom portion contains heavy fractions such as bicyclic aromatic hydrocarbons in addition to tricyclic aromatic hydrocarbons.

The catalyst separator 14 is configured to include, for example, a filter, and is a machine that separates the heavy fraction containing the catalyst derived from the cleaning tower 12 into solid and liquid, and separates and removes the catalyst from the heavy fraction. The separated catalyst may be, for example, sent to a catalyst regeneration tower (not illustrated), subjected to a regeneration treatment in the tower, and then recycled to the cracking and reforming reaction step, or, when significantly deteriorated, the catalyst may be disposed. The heavy fraction from which the catalyst has been removed, that is, polycyclic aromatic hydrocarbons, mainly tricyclic aromatic hydrocarbons, can be used as a fuel (torch oil) for, for example, heating the catalyst regeneration tower.

<Separation Step>

In the separation step (c), at least monocyclic aromatic hydrocarbons having 6 to 8 carbon atoms and a heavy fraction having 9 or more carbon atoms are separated from a derivative derived from the tower top portion of the cleaning tower 12 (catalyst separation step) using a plurality of separation apparatuses.

That is, the separation step is configured to include the first separation apparatus 16 and the debutanizer (second separation apparatus) 18 in the embodiment. However, the separation step of the embodiment does not necessarily include the above two separation apparatuses, and can also be made up of, for example, a sole distillation apparatus or the like. Therefore, it is also possible not to install the debutanizer (second separation apparatus) 18. In addition, the separation step may be configured to include a third separation apparatus 22 described below as necessary.

The first separation step 16 separates hydrogen, gas components such as methane and ethane, and a liquid fraction from the derivative. A well-known gas-liquid separation apparatus can be used as the first separation apparatus 16. Examples of the gas-liquid separation apparatus include an apparatus equipped with a gas-liquid separation tank, a production introduction tube through which a product is introduced into the gas-liquid separation tank, a gas component outflow tube provided in a top portion of the gas-liquid separation tank and a liquid component outflow tube provided in a bottom portion of the gas-liquid separation tank.

In the embodiment, two gas-liquid separation apparatuses are disposed, the liquid fraction is cooled in a former stage 16a so as to separate heavy fractions mainly containing tricyclic aromatic hydrocarbons (hereinafter referred to as tricyclic aromatic hydrocarbons), and the pressure is increased in a latter stage 16b, thereby separating the gas components and the liquid fraction from which the tricyclic aromatic hydrocarbons have been separated.

The debutanizer 18 (second separation apparatus) separates LPG fractions containing butane and the like and rough aromatic fractions containing a large amount of monocyclic aromatic hydrocarbons having 6 or more carbon atoms from the liquid fraction separated using the first separation apparatus 16.

<Tricyclic Aromatic Hydrocarbon Supply Step>

The tricyclic aromatic hydrocarbons separated in the former stage 16a (first separation apparatus 16) of the first separation apparatus 16 are returned to the cleaning tower 12 (catalyst separation step) as the cleaning liquid using a first returning line 24. That is, the tricyclic aromatic hydrocarbon supply step (e) in which the tricyclic aromatic hydrocarbons are supplied to the catalyst separation step as the cleaning liquid using the first returning line 24 is configured.

The tricyclic aromatic hydrocarbon supply step of the embodiment is not necessarily made up of only the first returning line 24, and, for example, may be made up of a second returning line 26 described below or both the first returning line 24 and the second returning line 26. Furthermore, it is also possible to separate the tricyclic aromatic hydrocarbons in any process behind the first separation apparatus 16 and to supply the hydrocarbons to the catalyst separation step as the cleaning liquid, and, in this case, a supply step of the tricyclic aromatic hydrocarbons also serves as the tricyclic aromatic hydrocarbon supply step.

When the tricyclic aromatic hydrocarbons are supplied to the cleaning tower 12 as the cleaning liquid, it is possible to clean the product in a mixed gas-liquid state in the cleaning tower 12, transfer the catalyst contained in the product to the cleaning liquid, efficiently separate and remove the catalyst from the product. Some of the tricyclic aromatic hydrocarbons supplied to the cleaning tower 12 are sent to the catalyst separator 14 together with the catalyst. In addition, the remaining hydrocarbons remain in the cleaning tower 12 or are sent to the first separation apparatus 16.

<Purification and Recovery Step>

The purification and recovery step (d) purifies and recovers the monocyclic aromatic hydrocarbons having 6 to 8 carbon atoms which are separated in the separation step using the purification and recovery apparatus 20.

The purification and recovery apparatus 20 separates monocyclic aromatic hydrocarbons having 6 to 8 carbon atoms (benzene/toluene/xylene) and the heavy fraction, that is, a fraction made up of, mainly, a heavy fraction having 9 or more carbon atoms from the rough aromatic fraction obtained using the debutanizer 18. In addition, the apparatus further purifies the separated monocyclic aromatic hydrocarbons having 6 to 8 carbon atoms, and respectively recovers benzene, toluene and xylene. A well-known distillation apparatus, for example, a multi-stage distillation apparatus, such as a stripper, can be used as the purification and recovery apparatus 20.

The third separation apparatus 22 separates a heavy fraction having 9 carbon atoms and a heavy fraction having 10 or more carbon atoms from the heavy fraction separated from the purification and recovery apparatus 20. In addition, the heavy fraction having 9 carbon atoms is recovered and used for a base material of a variety of products and the like. The heavy fraction having 10 or more carbon atoms is returned to the cracking and reforming reaction step, and sent to the recycling step in order to be provided to the cracking and reforming reaction in the cracking and reforming reactor 10 together with the feedstock oil. However, the third separation apparatus 22 is not an essential component in the embodiment, and the heavy fraction having 9 or more carbon atoms, which has been separated from the purification and recovery apparatus 20, may be sent to the recycling step without passing through the third separation apparatus.

Here, the heavy fraction separated from the monocyclic aromatic hydrocarbons having 6 to 8 carbon atoms in the purification and recovery apparatus 20 is a heavy fraction having 9 or more carbon atoms, and contains polycyclic aromatic hydrocarbons as a main component and a large amount of naphthalene and alkyl naphthalenes. In addition, the heavy fraction contains a small amount of tricyclic aromatic hydrocarbons. That is, tricyclic aromatic hydrocarbons that cannot be separated in the cleaning tower 12 and the first separation apparatus 16 are contained in the heavy fraction. Therefore, tricyclic aromatic hydrocarbons are separated in a form of a heavy fraction having 10 or more carbon atoms using the third separation apparatus 22.

As described above, the tricyclic aromatic hydrocarbons have a low reactivity in the cracking and reforming reaction step in spite of being a hydrogenation reaction product, and are rarely converted to monocyclic aromatic hydrocarbons, and therefore the tricyclic aromatic hydrocarbons do not contribute to the improvement of the reaction efficiency even when recycled in the cracking and reforming reaction step.

Therefore, it is also possible to let the third separation apparatus 22 not only separate the heavy fraction separated from the monocyclic aromatic recover apparatus 20 into a heavy fraction having 9 carbon atoms and a heavy fraction having 10 or more carbon atoms, but also separate tricyclic aromatic hydrocarbons from the heavy fraction having 9 or more carbon atoms. In addition, the separated tricyclic aromatic hydrocarbons are returned to the cleaning tower 12 (catalyst separation step) as the cleaning liquid using the second returning line 26. In this case, the second returning line 26 also configures the tricyclic aromatic hydrocarbon supply step in which the tricyclic aromatic hydrocarbons are supplied to the catalyst separation step as the cleaning liquid together with the first returning line 24 as described above.

However, the amount of tricyclic aromatic hydrocarbons separated using the third separation apparatus 22 is not large. Therefore, in consideration of an increase in the apparatus cost or the operation cost due to the separation of tricyclic aromatic hydrocarbons, in a case in which the economic effect of the separation and returning of tricyclic aromatic hydrocarbons is small, the step need not include the separation of tricyclic aromatic hydrocarbons using the third separation apparatus 22.

<Hydrogen Recovery Step>

In the hydrogen recovery step (f), hydrogen which is generated as a by-product in the cracking and reforming reaction step (cracking and reforming reactor 10) is recovered from the gas components separated in the separation step (the latter stage 16*b* of the first separation apparatus 16) using a hydrogen recovery apparatus 30.

A method for recovering hydrogen is not particularly limited as long as hydrogen contained in the gas components obtained in the separation step and other gases can be separated, and examples thereof include a pressure swing adsorption method (PSA method), a low temperature separation method, a membrane separation method and the like. Therefore, an apparatus that recovers hydrogen based on the above method (for example, a PSA apparatus) can be used as the hydrogen recovery apparatus 30.

Generally, the amount of hydrogen recovered in the hydrogen recovery step becomes larger than a necessary amount for hydrogenating the heavy fraction having 10 or more carbon atoms.

Other Embodiments

The first aspect of the invention is not limited to the first embodiment, and a variety of modifications can be made within the scope of the purpose of the invention.

In the first embodiment, tricyclic aromatic hydrocarbons are separated and removed in the catalyst separation step from the mixture derived from the cracking and reforming reaction step, and then the obtained heavy fraction having 10 or more carbon atoms is returned to the cracking and reforming reaction step. In this method, the heavy fraction returned to the cracking and reforming reaction step rarely contains tricyclic aromatic hydrocarbons which are not easily converted to monocyclic aromatic hydrocarbons in the cracking and reforming reaction step, and thus the conversion efficiency of the recycled heavy fraction (or the hydrogenation reaction product thereof) to monocyclic aromatic hydrocarbons improves. Therefore, the overall yield of monocyclic aromatic hydrocarbons with respect to the supply amount of the feedstock oil improves, and it is possible to increase the yield of monocyclic aromatic hydrocarbons having 6 to 8 carbon atoms.

In addition, since tricyclic aromatic hydrocarbons are separated in the separation step as well, it is possible to further decrease the content of tricyclic aromatic hydrocarbons in the recycled heavy fraction (or the hydrogenation reaction product thereof), and therefore it is possible to improve the conversion efficiency of the heavy fraction to monocyclic aromatic hydrocarbons.

In addition, since the tricyclic aromatic hydrocarbons separated in the separation step are supplied to the catalyst separation step as the cleaning liquid through the tricyclic aromatic hydrocarbon supply step using the first returning line 24 or the second returning line 26, it is possible to efficiently separate and remove the catalyst in the catalyst separation step.

Second Embodiment

An embodiment of a method for producing monocyclic aromatic hydrocarbons according to a second aspect of the invention will be described.

Figure 2:
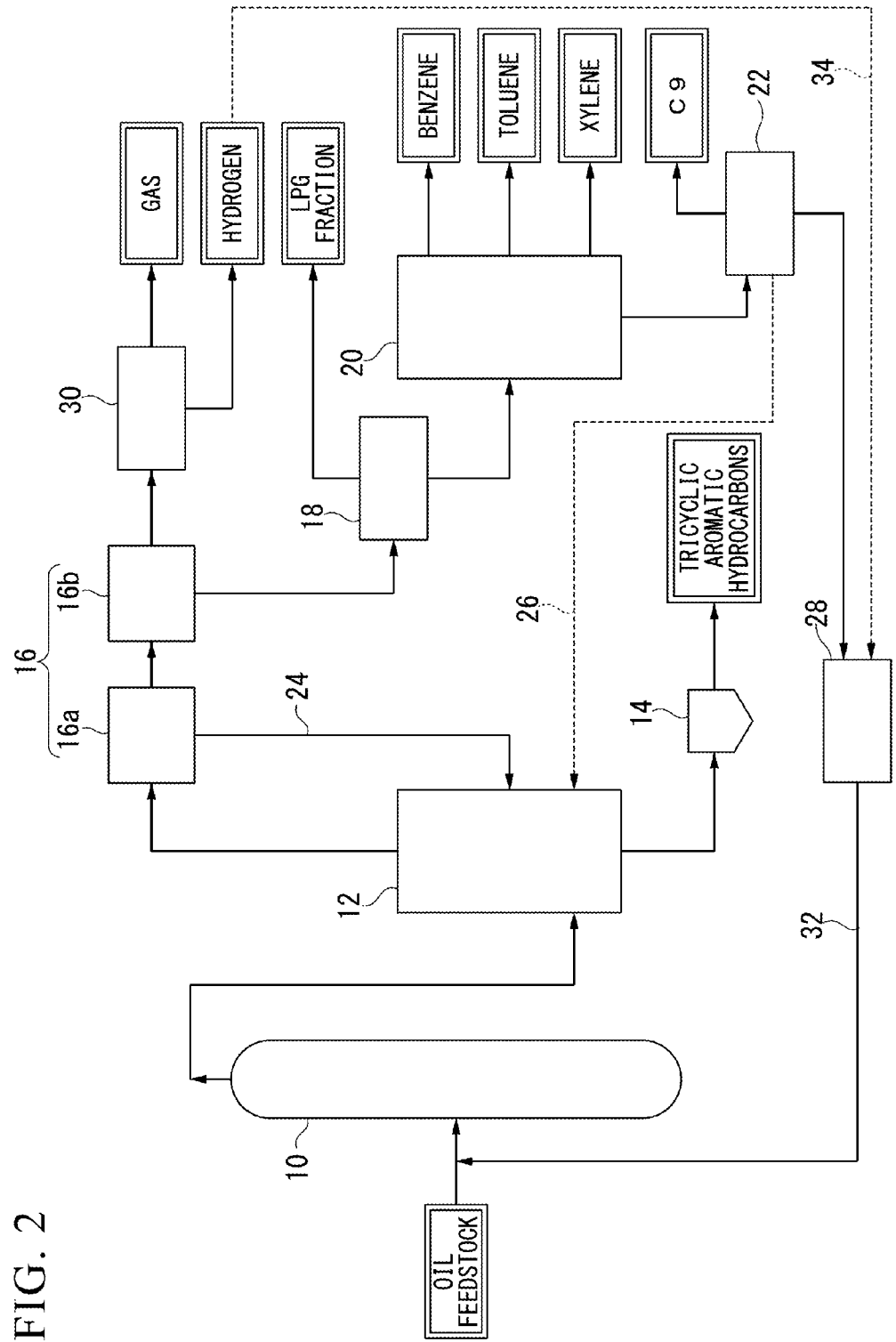
FIG. 2 is a schematic configuration view of a production plant for an embodiment (second embodiment) of a method for producing monocyclic aromatic hydrocarbons according to a second aspect of the invention.

The method for producing monocyclic aromatic hydrocarbons of the present embodiment is a method in which monocyclic aromatic hydrocarbons having 6 to 8 carbon atoms are produced from a feedstock oil, including the following steps (g) to (o). In addition, FIG. 2 is a schematic configuration view of a production plant for describing the second embodiment.

(g) A cracking and reforming reaction step of obtaining products containing monocyclic aromatic hydrocarbons having 6 to 8 carbon atoms and a heavy fraction having 9 or more carbon atoms by bringing a feedstock oil into contact with a catalyst for producing monocyclic aromatic hydrocarbons using the cracking and reforming reactor 10 to cause a reaction.

(h) A catalyst separation step of separating and removing the catalyst for producing monocyclic aromatic hydrocarbons together with tricyclic aromatic hydrocarbons contained in the products using the cleaning tower 12 and the catalyst separation apparatus 14 from a mixture of the products and the catalyst for producing monocyclic aromatic hydrocarbons carried by the products, both of which are derived in the cracking and reforming reaction step.

(i) A separation step of separating at least the monocyclic aromatic hydrocarbons (benzene/toluene/xylene) having 6 to 8 carbon atoms and a heavy fraction having 9 or more carbon atoms from a derivative derived in the catalyst separation step using the first separation apparatus 16 and the second separation apparatus 18, (j) A purification and recovery step of purifying and recovering the monocyclic aromatic hydrocarbons having 6 to 8 carbon atoms which are separated in the separation step using the purification and recovery apparatus 20.

(k) A hydrogenation reaction step of hydrogenating the heavy fraction having 9 or more carbon atoms which is separated in the separation step using a hydrogenation reactor 28.

(l) A recycling step of returning a hydrogenation reaction product of the heavy fraction having 9 or more carbon atoms obtained by the hydrogenation reaction step to the cracking and reforming reaction step using a recycling line 32.

(m) A tricyclic aromatic hydrocarbon supply step of supplying tricyclic aromatic hydrocarbons separated from the derivative which is derived in the catalyst separation step to the catalyst separation step using the returning lines 24 and 26 in the separation step.

(n) A hydrogen recovery step of recovering hydrogen which is generated as a by-product in the cracking and reforming reaction step from gas components separated in the separation step using the hydrogen recovery apparatus 30.

(o) A hydrogen supply step of supplying hydrogen recovered in the hydrogen recovery step to the hydrogenation reaction step using a hydrogen supply line 34.

Among the steps (g) to (o), the steps (g), (h), (i), (j) and (l) are the essential steps of the second aspect, and the steps (k), (m), (n) and (o) are arbitrary steps. Therefore, in the recycling step (l), it is also possible to directly return the heavy fraction having 9 or more carbon atoms which is separated in the separation step to the cracking and reforming reaction step without passing through the hydrogenation reaction step.

Hereinafter, the respective steps will be specifically described.

<Cracking and Reforming Reaction Step>

The cracking and reforming reaction step (g) can be carried out in the same manner as the cracking and reforming reaction step (a) in the first embodiment.

<Catalyst Separation Step>

The catalyst separation step (h) can be carried out in the same manner as the catalyst separation step (b) in the first embodiment.

<Separation Step>

The separation step (i) can be carried out in the same manner as the separation step (c) in the first embodiment.

<Tricyclic Aromatic Hydrocarbon Supply Step>

The tricyclic aromatic hydrocarbon supply step (m) can be carried out in the same manner as the tricyclic aromatic hydrocarbon supply step (e) in the first embodiment.

<Purification and Recovery Step>

The purification and recovery step (j) can be carried out in the same manner as the purification and recovery step (d) in the first embodiment.

<Hydrogenation Reaction Step>

In the hydrogenation reaction step (k), the heavy fraction having 10 or more carbon atoms which is separated in the third separation apparatus 22 (separation step) is hydrogenated using the hydrogenation reactor 28. Specifically, the heavy fraction and hydrogen are supplied to the hydrogenation reactor 28, and at least some of polycyclic aromatic hydrocarbons (mainly bicyclic aromatic hydrocarbons) contained in the heavy fraction are hydrogenated using a hydrogenation catalyst.

The polycyclic aromatic hydrocarbons are preferably hydrogenated until only one aromatic ring remains.

For example, naphthalene is preferably hydrogenated until the naphthalene turns into tetralin (naphthenobenzene). When the polycyclic aromatic hydrocarbons are hydrogenated until only one aromatic ring remains, the polycyclic aromatic hydrocarbons are easily converted to monocyclic aromatic hydrocarbons when returned to the cracking and reforming reaction step (cracking and reforming reactor 10).

In addition, in order to improve the yield of monocyclic aromatic hydrocarbons in the cracking and reforming reaction step, in the hydrogenation reaction step, the content of the polycyclic aromatic hydrocarbons in the hydrogenation reaction product of the obtained heavy fraction is preferably set to 40% by mass or less, more preferably set to 25% by mass or less, and still more preferably set to 15% by mass or less. The content of the polycyclic aromatic hydrocarbons in the hydrogenation reaction product is preferably smaller than the content of polycyclic aromatic hydrocarbons in the feedstock oil, and can be decreased by increasing the amount of hydrogenation catalyst or the reaction pressure. However, it is not necessary to hydrogenate the heavy fraction until all the polycyclic aromatic hydrocarbons turn into saturated hydrocarbons. There is a tendency that excessive hydrogenation leads to an increase in the consumption amount of hydrogen and an increase in the amount of heat generation.

In the embodiment, hydrogen generated as a byproduct in the cracking and reforming reaction step (cracking and reforming reactor 10) is used as the hydrogen. That is, hydrogen is recovered using the hydrogen recovery step (hydrogen recovery apparatus 30) described below from the gas components obtained in the separation step (first separation apparatus 16), and the recovered hydrogen is supplied to the hydrogenation reaction step (hydrogenation reactor 28) using the hydrogen supply step (hydrogen supply line 34).

A preferable example of the reaction type of the hydrogenation reactor 28 (hydrogenation reaction step) is a fixed bed.

As the hydrogenation catalyst, a well-known hydrogenation catalyst (for example, a nickel catalyst, a palladium catalyst, a nickel-molybdenum-based catalyst, a cobalt-molybdenum-based catalyst, a nickel-cobalt-molybdenum-based catalyst, a nickel-tungsten-based catalyst or the like) can be used.

The hydrogenation reaction temperature differs depending on the hydrogenation catalyst used, and is generally in a range of 100° C. to 450° C., more preferably in a range of 200° C. to 400° C., and still more preferably in a range of 250° C. to 380° C.

The hydrogenation reaction pressure differs depending on the hydrogenation catalyst or raw material used, but is preferably set in a range of 0.7 MPa to 13 MPa, more preferably set in a range of 1 MPa to 10 MPa, and particularly preferably set in a range of 1 MPa to 7 MPa. When the hydrogenation reaction pressure is set to 13 MPa or less, it is possible to use a hydrogenation reactor with a low pressure resistance, which can decrease the facility cost.

On the other hand, the hydrogenation reaction pressure is preferably 0.7 MPa or more in terms of the yield of the hydrogenation reaction.

The consumption amount of hydrogen is preferably 3000 scfb (506 Nm$^3$/m$^3$) or less, more preferably 2500 scfb (422 Nm$^3$/m$^3$) or less, and still more preferably 1500 scfb (253 Nm$^3$/m$^3$) or less.

On the other hand, the consumption amount of hydrogen is preferably 300 scfb (50 Nm$^3$/m$^3$) or more in terms of the yield of the hydrogenation reaction.

The liquid hourly space velocity (LHSV) of the heavy fraction is preferably set in a range of 0.1 h$^{-1}$ to 20 h$^{-1}$, and more preferably set in a range of 0.2 h$^{-1}$ to 10 h$^{-1}$. When LHSV is set to 20 h$^{-1}$ or less, the polycyclic aromatic hydrocarbons can be sufficiently hydrogenated at a lower hydrogenation reaction pressure. On the other hand, when LHSV is set to 0.1 h$^{-1}$ or more, it is possible to prevent an increase in the size of the hydrogenation reactor.

<Recycling Step>

In the recycling step (l), the hydrogenation reaction product of the heavy fraction obtained in the hydrogenation reaction step and the feedstock oil are returned to the cracking and reforming reaction step in a form of a mixture with the feedstock oil produced using the recycling line 32 or separately from the feedstock oil.

When the hydrogenation reaction product of the heavy fraction is returned to the cracking and reforming reaction step, monocyclic aromatic hydrocarbons can be obtained using the heavy fraction which has been a byproduct as a raw material. Therefore, the amount of byproduct can be decreased so that it is possible to increase the generation amount of monocyclic aromatic hydrocarbons, whereby the production efficiency of monocyclic aromatic hydrocarbons having 6 to 8 carbon atoms can be increased. In addition, since hydrogenation also generates saturated hydrocarbons, it is also possible to accelerate a hydrogen transfer reaction in the cracking and reforming reaction step.

Furthermore, since the hydrogenation reaction product of the heavy fraction returned to the cracking and reforming reaction step in the recycling step (recycling line 32) rarely contains tricyclic aromatic hydrocarbons that are not easily converted to monocyclic aromatic hydrocarbons in the cracking and reforming reaction step, the conversion efficiency of the recycled hydrogenation reaction product to monocyclic aromatic hydrocarbons improves.

Based on what has been described above, the overall yield of monocyclic aromatic hydrocarbons with respect to the supply amount of the feedstock oil improves, and therefore it is possible to increase the yield of monocyclic aromatic hydrocarbons having 6 to 8 carbon atoms.

In the recycling step, it is not necessary to recycle the entire hydrogenation reaction product to the feedstock oil of the cracking and reforming reaction step at all times. In this case, the hydrogenation reaction product which is not recycled can be used as, for example, a base fuel material.

In addition, in the embodiment, the heavy fraction having 10 or more carbon atoms obtained using the third separation apparatus 22 (separation step) is returned to the cracking and reforming reaction step after being hydrogenated, but the heavy fraction may be returned to the cracking and reforming reaction step with no hydrogenation treatment. In this case as well, since the recycled oil rarely contains tricyclic aromatic hydrocarbons, the conversion efficiency of the recycled oil to monocyclic aromatic hydrocarbons improves.

In addition, the heavy fraction having 9 or more carbon atoms separated from the purification and recovery apparatus 20 may be directly provided to the hydrogenation reactor 28 (hydrogenation reaction step) or the cracking and reforming reactor 10 (cracking and reforming reaction step) without separating the heavy fraction separated from the purification and recovery apparatus 20 into the heavy fraction having 9 carbon atoms and the heavy fraction having 10 or more carbon atoms using the third separation apparatus 22.

<Hydrogen Recovery Step>

In the hydrogen recovery step (n), hydrogen generated as a byproduct in the cracking and reforming reaction step (cracking and reforming reactor 10) is recovered from the gas components obtained in the separation step (the latter stage 16*b* of the first separation apparatus 16) using the hydrogen recovery apparatus 30.

A method for recovering hydrogen is not particularly limited as long as hydrogen contained in the gas components obtained in the separation step and other gases can be separated, and examples thereof include a pressure swing adsorption method (PSA method), a low temperature separation method, a membrane separation method and the like. Therefore, an apparatus that recovers hydrogen based on the above method (for example, a PSA apparatus) can be used as the hydrogen recovery apparatus 30.

Generally, the amount of hydrogen recovered in the hydrogen recovery step becomes larger than a necessary amount for hydrogenating the heavy fraction having 9 or more carbon atoms.

<Hydrogen Supply Step>

In the hydrogen supply step (o), the hydrogen obtained in the hydrogen recovery step (hydrogen recovery apparatus 30) is supplied to the hydrogenation reaction step (hydrogenation reactor 28) using the hydrogen supply line 34. The supply amount of hydrogen at this time is adjusted depending on the amount of heavy fraction supplied to the hydrogenation reaction step. In addition, the pressure of the hydrogen is adjusted as necessary.

When the hydrogen supply step of the embodiment is provided, the heavy fraction can be hydrogenated using the hydrogen generated as a byproduct in the cracking and reforming reaction step (cracking and reforming reactor 10). Therefore, it is possible to decrease some or all of hydrogen supplied from an external source by supplying some or all of hydrogen used in the production method of the embodiment using hydrogen generated as a byproduct.

In the method for producing monocyclic aromatic hydrocarbons of the embodiment, monocyclic aromatic hydrocarbons can be obtained using the heavy fraction produced as a byproduct as a raw material by returning the heavy fraction having 10 or more carbon atoms or the heavy fraction having 9 or more carbon atoms to the cracking and reforming reaction step. Therefore, the amount of byproduct can be decreased so that it is possible to increase the generation amount of monocyclic aromatic hydrocarbons, whereby the production efficiency of monocyclic aromatic hydrocarbons having 6 to 8 carbon atoms can be increased.

In addition, when the heavy fraction is hydrogenated in the hydrogenation reaction step and returned to the cracking and reforming reaction step, hydrogenation also generates saturated hydrocarbons, and therefore it is also possible to accelerate the hydrogen transfer reaction in the cracking and reforming reaction step.

Furthermore, since tricyclic aromatic hydrocarbons are separated and removed from the mixture derived from the cracking and reforming reaction step in the catalyst separation step, and the subsequently obtained heavy fraction having 10 (9) or more carbon atoms is returned to the cracking and reforming reaction step, the heavy fraction returned to the cracking and reforming reaction step rarely contains tricyclic aromatic hydrocarbons that are not easily converted to monocyclic aromatic hydrocarbons in the cracking and reforming reaction step, the conversion efficiency of the recycled heavy fraction (or the hydrogenation reaction product thereof) to monocyclic aromatic hydrocarbons improves. Therefore, the overall yield of monocyclic aromatic hydrocarbons with respect to the supply amount of the feedstock oil improves, and it is possible to increase the yield of monocyclic aromatic hydrocarbons having 6 to 8 carbon atoms.

In addition, since tricyclic aromatic hydrocarbons are also separated in the separation step, it is possible to decrease the content of tricyclic aromatic hydrocarbons in the recycled heavy fraction (or the hydrogenation reaction product thereof), and therefore it is possible to improve the conversion efficiency of the heavy fraction to monocyclic aromatic hydrocarbons.

In addition, since the tricyclic aromatic hydrocarbons separated in the separation step are supplied to the catalyst separation step as the cleaning liquid through the tricyclic aromatic hydrocarbon supply step using the first returning line 24 or the second returning line 26, it is possible to efficiently separate and remove the catalyst in the catalyst separation step.

Third Embodiment

Another embodiment of the method for producing monocyclic aromatic hydrocarbons according to the second aspect of the invention will be described.

Figure 3:
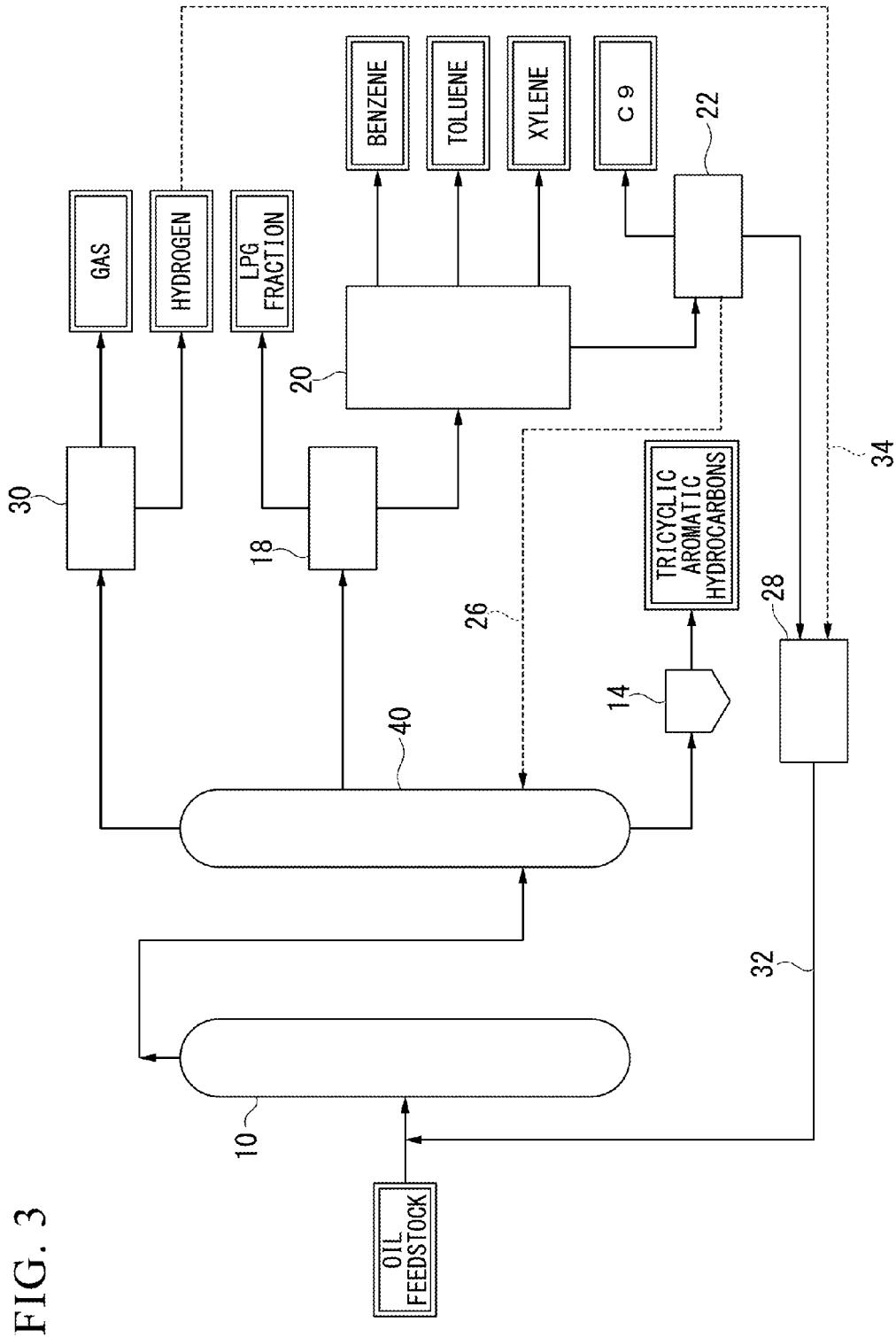
FIG. 3 is a schematic configuration view of a production plant for an embodiment (third embodiment) of a method for producing monocyclic aromatic hydrocarbons according to a second aspect of the invention.

FIG. 3 is a schematic configuration view of a production plant for describing the third embodiment. Similarly to the second embodiment, the method for manufacturing monocyclic aromatic hydrocarbons of the embodiment is a method in which monocyclic aromatic hydrocarbons having 6 to 8 carbon atoms are produced from a raw material.

The differences between the third embodiment and the second embodiment illustrated in FIG. 2 are as follows. While the cleaning step is made up of the cleaning tower 12 and the catalyst separator 16, and the separation step is made up of the first separation apparatus 16, the debutanizer 18 (second separation apparatus), the purification and recovery apparatus 20 and the third separation apparatus 22 in the second embodiment, the cleaning step is made up of a fractionator 40 and a catalyst separator 14, and the separation step is made up of the fractionator 40, the debutanizer 18 (second separation apparatus), the purification and recovery apparatus 20 and the third separation apparatus 22 in the third embodiment as illustrated in FIG. 3. That is, in the embodiment, the fractionator 40 is used instead of the cleaning tower 12 and the first separation apparatus 16 in the second embodiment.

Therefore, similarly to the second embodiment, basically, the method for producing monocyclic aromatic hydrocarbons of the embodiment is a method including the steps (g) to (o).

Hereinafter, steps in which different apparatuses from the second embodiment are used will be described. The same steps that use the same apparatuses as those used in the second embodiment will not be described.

<Catalyst Separation Step>

In the catalyst separation step, similarly to the second embodiment, the catalyst (catalyst for producing monocyclic aromatic hydrocarbons) is removed from the mixture derived from the cracking and reforming reaction step (cracking and reforming reactor 10).

In addition, the tricyclic aromatic hydrocarbons contained in the product obtained in the cracking and reforming reaction step are also separated and removed.

However, in the embodiment, the fractionator 40 functions as the cleaning tower 12 in the second embodiment. The fractionator 40 is a well-known distillation tower made up of multiple phases in which the catalyst in the mixture or the heavy fraction mainly containing tricyclic aromatic hydrocarbons is separated in the tower bottom portion and the gas components in the mixture (the product of the cracking and reforming reaction step) is separated in the tower top portion. In addition, an intermediate fraction (liquid fraction) between the gas components and the heavy fraction mainly containing tricyclic aromatic hydrocarbons is separated in a middle portion.

In the tower bottom portion of the fractionator 40, the heavy fraction having a high boiling point, that is, the heavy fraction mainly containing tricyclic aromatic hydrocarbons is liquefied. Then, the heavy fraction mainly containing tricyclic aromatic hydrocarbons is derived from the tower bottom portion together with the catalyst.

The derived heavy fraction is supplied to the catalyst separator 14, similarly to the second embodiment, and the catalyst is separated and removed in the catalyst separator. In addition, the polycyclic aromatic hydrocarbons (heavy fraction) mainly containing tricyclic aromatic hydrocarbons from which the catalyst has been removed are used as, for example, a fuel (torch oil) for heating the catalyst regeneration tower.

\<Separation Step\>

In addition, from a middle portion to a tower top portion of the fractionator 40, similarly to the first separation apparatus 16 in the second embodiment, hydrogen, gas components such as methane and ethane, and a liquid fraction are separated from the fraction from which the catalyst has been removed (derivative) using a distillation operation. In addition, the intermediate fraction (liquid fraction) separated from the middle portion as described above is derived, and the gas components are derived from the tower top portion.

When the gas components and the liquid fraction have been separated from the middle portion to the tower top portion of the fractionator 40, tricyclic aromatic hydrocarbons are liquefied as a part of the liquid fraction. The liquefied tricyclic aromatic hydrocarbons are made to flow down to the tower bottom portion as a heavy fraction, and function as a cleaning liquid for catalyst separation carried out in the tower bottom portion. Therefore, the fractionator 40 also includes the tricyclic aromatic hydrocarbon supply step inside.

The intermediate fraction (liquid fraction) derived from the middle portion of the fractionator 40 is supplied to the debutanizer 18 (second separation apparatus) so as to be separated, and then, similarly to the second embodiment, the intermediate fraction is sequentially separated using the purification and recovery apparatus 20 and the third separation apparatus 22. In addition, the heavy fraction having 10 or more carbon atoms is sent to the hydrogenation reaction step (hydrogenation reactor 28) so as to be provided to a hydrogenation reaction, and then returned to the cracking and reforming reaction step in a form of a mixture with the feedstock oil produced using the recycling step (recycling line 32) or separately from the feedstock oil. In a case in which tricyclic aromatic hydrocarbons (the heavy fraction mainly containing tricyclic aromatic hydrocarbons) are separated from the heavy fraction having 10 or more carbon atoms in the third separation apparatus 22, the separated tricyclic aromatic hydrocarbons are returned to the tower bottom portion of the fractionator 40 as the cleaning liquid through the second returning line 26. In addition, the embodiment need not include the third separation apparatus 22.

The gas components derived from the tower top portion of the fractionator 40 are sent to the hydrogen recovery apparatus 30 (hydrogen recovery step), and then treated in the same manner as in the second embodiment.

In the method for producing monocyclic aromatic hydrocarbons of the embodiment as well, monocyclic aromatic hydrocarbons can be obtained using the heavy fraction produced as a byproduct as a raw material by returning the heavy fraction having 10 or more carbon atoms or the heavy fraction having 9 or more carbon atoms to the cracking and reforming reaction step. Therefore, the amount of byproduct can be decreased so that it is possible to increase the generation amount of monocyclic aromatic hydrocarbons, whereby the production efficiency of monocyclic aromatic hydrocarbons having 6 to 8 carbon atoms can be increased.

In addition, when the heavy fraction is hydrogenated in the hydrogenation reaction step and returned to the cracking and reforming reaction step, hydrogenation also generates saturated hydrocarbons, and therefore it is also possible to accelerate the hydrogen transfer reaction in the cracking and reforming reaction step.

Furthermore, tricyclic aromatic hydrocarbons are separated and removed from the mixture derived from the cracking and reforming reaction step in the catalyst separation step, and the subsequently obtained heavy fraction having 10 (9) or more carbon atoms is returned to the cracking and reforming reaction step. In this method, the heavy fraction returned to the cracking and reforming reaction step rarely contains tricyclic aromatic hydrocarbons that are not easily converted to monocyclic aromatic hydrocarbons in the cracking and reforming reaction step, and therefore the conversion efficiency of the recycled heavy fraction (or the hydrogenation reaction product thereof) to monocyclic aromatic hydrocarbons improves. Therefore, the overall yield of monocyclic aromatic hydrocarbons with respect to the supply amount of the feedstock oil improves, and it is possible to increase the yield of monocyclic aromatic hydrocarbons having 6 to 8 carbon atoms.

In addition, since tricyclic aromatic hydrocarbons are also separated in the separation step, it is possible to decrease the content of tricyclic aromatic hydrocarbons in the recycled heavy fraction (or the hydrogenation reaction product thereof), and therefore it is possible to improve the conversion efficiency of the heavy fraction to monocyclic aromatic hydrocarbons.

Other Embodiments

The second aspect of the invention is not limited to the second or third embodiment, and a variety of modifications can be made within the scope of the purpose of the invention.

For example, the hydrogen used in the hydrogenation reaction step is not necessarily hydrogen generated as a byproduct in the cracking and reforming reaction step, and hydrogen obtained using a well-known method for producing hydrogen may be used, or hydrogen generated as a byproduct using other catalytic reforming methods may be used.

The recycled heavy fraction may be introduced into the cracking reaction step after being directly mixed with the feedstock oil as described above or may be introduced separately from the feedstock oil.

EXAMPLES

Example 1

In the production plant illustrated in FIG. 1, LCO having the same properties as in Comparison Test Example 1 was provided to a cracking and reforming reactor as a feedstock oil, and a reaction was allowed to proceed. Then, the same treatments as in the first embodiment were carried out, BTX were produced through a 5-hour-long test, and it was confirmed that a heavy fraction having 10 or more carbon atoms could be derived from the third separation apparatus 22.

Comparison Test Example 1

In the production plant illustrated in FIG. 2, LCO having properties described in the following table was provided to the cracking and reforming reactor 10 as a feedstock oil, and a reaction was allowed to proceed. Then, the same treatments as in the second embodiment were carried out, and a heavy fraction from which a catalyst had been removed using the catalyst separator 14, that is, polycyclic aromatic hydrocarbons, mainly tricyclic aromatic hydrocarbons were recovered. In addition, the recovered heavy fraction was provided to the hydrogenation reactor 28 so as to cause a hydrogenation reaction, thereby obtaining a hydrogenation reaction product of the heavy fraction. After that, the obtained hydrogenation reaction product was provided to the cracking and reforming reactor 10 instead of the feedstock oil, and a cracking and reforming reaction was allowed to proceed. As a result of investigating the amount (content rate) of tricyclic aromatic hydrocarbons in the heavy fraction, the amount was approximately 42.8% by mass, and the majority of the remainder was bicyclic aromatic hydrocarbons.

TABLE 1

| Properties of raw material | | | | Analysis method |
|---|---|---|---|---|
| Density (measurement temperature of 15° C.) | | g/cm³ | 0.906 | JIS K 2249 |
| Kinetic viscosity (measurement temperature of 30° C.) | | mm²/s | 3.640 | JIS K 2283 |
| Distillation properties | Initial boiling point | ° C. | 175.5 | JIS K 2254 |
| | 10 volume percent distillation temperature | ° C. | 224.5 | |
| | 50 volume percent distillation temperature | ° C. | 274.0 | |
| | 90 volume percent distillation temperature | ° C. | 349.5 | |
| | End point | ° C. | 376.0 | |
| Composition analysis | Saturated component | % by volume | 35 | JPI-5S-49 |
| | Olefin component | % by volume | 8 | |
| | Wholly aromatic component | % by volume | 57 | |
| | Monocyclic aromatic component | % by volume | 23 | |
| | Bicyclic aromatic component | % by volume | 25 | |
| | Tri- or more-cyclic aromatic component | % by volume | 9 | |

Example 2

In the production plant illustrated in FIG. 2, LCO having the same properties as in Comparison Test Example 1 was provided to the cracking and reforming reactor 10 as a feedstock oil, and a reaction was allowed to proceed. Then, the same treatments as in the second embodiment were carried out, and a heavy fraction having 10 or more carbon atoms derived from the third separation apparatus 22 was recovered. In addition, the recovered heavy fraction was provided to the hydrogenation reactor 28 so as to cause a hydrogenation reaction, thereby obtaining a hydrogenation reaction product of the heavy fraction. After that, the obtained hydrogenation reaction product was provided to the cracking and reforming reactor 10 instead of the feedstock oil, and a cracking and reforming reaction was allowed to proceed. In the third separation apparatus 22, the recovered heavy fraction was supplied to the cracking and reforming reactor 10 without separating tricyclic aromatic hydrocarbons. As a result of investigating the amount (content rate) of tricyclic aromatic hydrocarbons in the heavy fraction, the amount was approximately 3.1% by mass, and the majority of the remainder was bicyclic aromatic hydrocarbons.

Comparison Test Example 2

The heavy fraction recovered after removing the catalyst using the catalyst separator 14 in Comparison Test Example 1 and the heavy fraction having 10 or more carbon atoms which had been derived from the third separation apparatus 22 and derived in Example 2 were mixed. In addition, the heavy fraction mixture was provided to the hydrogenation reactor 28 so as to cause a hydrogenation reaction, thereby obtaining a hydrogenation reaction product of the heavy fraction mixture. After that, the obtained hydrogenation reaction product was provided to the cracking and reforming reactor 10 instead of the feedstock oil, and a cracking and reforming reaction was allowed to proceed. The mixing ratio (mass ratio) (Comparison Test Example 1 versus Example 2) between the heavy fraction used in Comparison Test Example 1 and the heavy fraction used in Example 2 was set to approximately 1:9. Therefore, in the computation, the amount (content rate) of tricyclic aromatic hydrocarbons in the heavy fraction mixture became approximately 7.0% by mass.

Comparison Test Example 3

LCO having the same properties as in Comparison Test Example 1 and Example 2 was supplied to the cracking and reforming reactor 10 as a feedstock oil.

In Comparison Test Example 1, Example 2, Comparison Test Example 2 and Comparison Test Example 3, the BTX (benzene, toluene and xylene) in the respective products obtained after causing the cracking and reforming reaction in the cracking and reforming reactor 10, that is, the BTX yields were investigated. The results will be described below. The units of the following BTX yields are % by mass.

TABLE 2

| | Comparison Test Example 1 | Example 2 | Comparison Test Example 2 | Comparison Test Example 3 |
|---|---|---|---|---|
| (3RA) | (42.8) | (3.1) | (7.0) | (—) |
| BTX yield | 26% | 48% | 45% | 37% |

Here, (3RA) represents tricyclic aromatic hydrocarbons, and the numeric value in parentheses represents the amount (content rate) of tricyclic aromatic hydrocarbons in the heavy fraction before the hydrogenation reaction used in each of the examples.

The results show that the BTX yield was far lower in Comparison Test Example 1 than in Comparison Test Example 3 even though the heavy fraction mainly containing tricyclic aromatic hydrocarbon from which the catalyst had been removed using the catalyst separator 14 was supplied to the cracking and reforming reactor 10 after a hydrogenation reaction. Therefore, it was found that it is not preferable to use the heavy fraction from which the catalyst is removed using the catalyst separator 14 as a recycled oil.

In Example 2 in which the heavy fraction having 10 or more carbon atoms which had been derived from the third separation apparatus 22 and recovered was supplied to the cracking and reforming reactor 10 after the hydrogenation reaction and a cracking and reforming reaction was carried out, the BTX yield sufficiently improved compared with Comparison Test Example 3. Furthermore, it was found that the BTX yield sufficiently improves compared with Comparison Test Example 2. In Comparison Test Example 2, the separated heavy fraction mainly containing tricyclic aromatic hydrocarbons was mixed with the heavy fraction having 10 or more carbon atoms derived from the third separation apparatus 22 and recovered, and the BTX yield was higher in Example 2 than in Comparison Test Example 2, which indicated that the BTX yield improves when the heavy fraction mainly containing tricyclic aromatic hydrocarbons is removed.

Therefore, it was confirmed that, when tricyclic aromatic hydrocarbons were removed using the catalyst separator 14 together with the catalyst, and the heavy fraction having 10 or more carbon atoms derived from the third separation apparatus 22 and recovered was provided to the cracking and reforming reaction step as a recycled oil together with a feedstock oil, it was possible to improve the BTX yield compared with a case in which only the feedstock oil was provided to the cracking and reforming reaction step (Comparison Test Example 3).

INDUSTRIAL APPLICABILITY

The invention is useful for the production of monocyclic aromatic hydrocarbons using LCO obtained from an FCC apparatus and kerosene, a light oil or the like obtained from a crude distillation apparatus as a raw material.

REFERENCE SIGNS LIST

10 CRACKING AND REFORMING REACTOR
12 CLEANING TOWER
14 CATALYST SEPARATION APPARATUS
16 FIRST SEPARATION APPARATUS
18 DEBUTANIZER (SECOND SEPARATION APPARATUS)
20 PURIFICATION AND RECOVERY APPARATUS
22 THIRD SEPARATION APPARATUS
24 FIRST RETURNING LINE
26 SECOND RETURNING LINE
28 HYDROGENATION REACTOR
30 HYDROGEN RECOVERY APPARATUS
32 RECYCLING LINE
34 HYDROGEN SUPPLY LINE
40 FRACTIONATOR

The invention claimed is:

1. A method for producing monocyclic aromatic hydrocarbons, the method comprising:
preparing a feedstock oil having a 10 volume percent distillation temperature of 140° C. or higher and a 90 volume percent distillation temperature of 380° C. or lower;
contacting the feedstock oil with a catalyst containing crystalline aluminosilicate to cause a reaction in a cracking and reforming reactor;
removing a mixture comprising the catalyst and a first effluent comprising monocyclic aromatic hydrocarbons having 6 to 8 carbon atoms and tricyclic aromatic hydrocarbons;
supplying the mixture and a cleaning liquid to a cleaning tower, wherein the cleaning liquid is injected to a top portion of the cleaning tower;
separating the catalyst from the mixture and removing the catalyst from a bottom portion of the cleaning tower;
recovering a second effluent stream including the monocyclic aromatic hydrocarbons having 6 to 8 carbon atoms and at least a portion of tricyclic aromatic hydrocarbons from a top portion of the cleaning tower;
cooling the second effluent stream to separate a tricyclic aromatic fraction and a liquid fraction, where the tricyclic aromatic fraction comprises a majority of the tricyclic aromatic hydrocarbons from the second effluent stream;
recycling the tricyclic aromatic fraction to the cleaning tower as the cleaning liquid;
compressing the liquid fraction to recover a stream comprising gas components and a second liquid fraction;
separating the second liquid fraction into a product stream comprising monocyclic aromatic hydrocarbons having 6 to 8 carbon atoms and a residual fraction having 9 or more carbon atoms;
separating the residual fraction into a fraction having 9 carbon atoms and a fraction having 10 or more carbon atoms; and
returning the fraction having 10 or more carbon atoms to the cracking and reforming reactor.

2. A method for producing monocyclic aromatic hydrocarbons having 6 to 8 carbon atoms, the method comprising:
preparing a feedstock oil having a 10 volume percent distillation temperature of 140° C. or higher and a 90 volume percent distillation temperature of 380° C. or lower;
contacting the feedstock oil with a catalyst containing crystalline aluminosilicate to cause a reaction in a cracking and reforming reactor;
removing a mixture comprising the catalyst and a first effluent comprising monocyclic aromatic hydrocarbons having 6 to 8 carbon atoms and tricyclic aromatic hydrocarbons;
supplying the mixture and a cleaning liquid to a cleaning tower, wherein the cleaning liquid is injected to a top portion of the cleaning tower;
separating the catalyst from the mixture and removing the catalyst from a bottom portion of the cleaning tower;
recovering a second effluent stream including the monocyclic aromatic hydrocarbons having 6 to 8 carbon atoms and at least a portion of tricyclic aromatic hydrocarbons from a top portion of the cleaning tower;
cooling the second effluent stream to separate a tricyclic aromatic fraction and a liquid fraction, where the tricyclic aromatic fraction comprises a majority of the tricyclic aromatic hydrocarbons from the second effluent stream;
recycling the tricyclic aromatic fraction to the cleaning tower as the cleaning liquid;
compressing the liquid fraction to recover a stream comprising gas components and a second liquid fraction;
separating the second liquid fraction into a product stream comprising monocyclic aromatic hydrocarbons having 6 to 8 carbon atoms and a residual fraction having 9 or more carbon atoms;
separating the residual fraction into a fraction having 9 carbon atoms and a fraction having 10 or more carbon atoms;
hydrogenating the fraction having 10 or more carbon atoms; and returning the fraction having 10 or more carbon atoms to the cracking and reforming reactor.

3. The method for producing monocyclic aromatic hydrocarbons according to claim 2, further comprising:
recovering hydrogen which is generated as a by-product during the cracking and reforming reaction; and
supplying the hydrogen to the hydrogenating of the fraction having 10 or more carbon atoms.

4. The method for producing monocyclic aromatic hydrocarbons according to claim 1, further comprising:
recovering a tower bottom liquid from the cleaning tower, where the tower bottom liquid comprises the tricyclic aromatic hydrocarbons after being used as a cleaning liquid;
cooling the tower bottom liquid recovered from the cleaning tower by using a heat exchanger;
supplying the cooled tower bottom liquid to a middle of the cleaning tower;

making a countercurrent contact between the cooled tower bottom liquid and a vapor of the products; and trapping the catalyst by the cooled tower bottom liquid.

5. The method for producing monocyclic aromatic hydrocarbons according to claim 2, further comprising:

recovering a tower bottom liquid from the cleaning tower, where the tower bottom liquid comprises the tricyclic aromatic hydrocarbons after being used as a cleaning liquid;

cooling the tower bottom liquid recovered from the cleaning tower by using a heat exchanger;

supplying the cooled tower bottom liquid to a middle of the cleaning tower;

making a countercurrent contact between the cooled tower bottom liquid and a vapor of the products; and trapping the catalyst by the cooled tower bottom liquid.

* * * * *